(12) United States Patent
Howlett et al.

(10) Patent No.: US 10,086,136 B2
(45) Date of Patent: Oct. 2, 2018

(54) METHOD FOR CONTROLLING DRUG DELIVERY THROUGH AN INFUSION SET

(71) Applicant: CareFusion Corporation, San Diego, CA (US)

(72) Inventors: Michael Wallace Howlett, Salt Lake City, UT (US); James Victor Mercer, West Jordan, UT (US)

(73) Assignee: CAREFUSION CORPORATION, San Diego, CA (US)

( * ) Notice: Subject to any disclaimer, the term of this patent is extended or adjusted under 35 U.S.C. 154(b) by 200 days.

(21) Appl. No.: 15/013,963

(22) Filed: Feb. 2, 2016

(65) Prior Publication Data

US 2016/0151567 A1 Jun. 2, 2016

Related U.S. Application Data (60) Continuation of application No. 13/777,747, filed on Feb. 26, 2013, now Pat. No. 9,272,129, which is a division of application No. 12/142,448, filed on Jun. 19, 2008, now Pat. No. 8,403,291.

(60) Provisional application No. 60/936,351, filed on Jun. 21, 2007.

(51) Int. Cl.
*A61M 5/168* (2006.01)
*A61M 39/28* (2006.01)
*A61M 5/142* (2006.01)

(52) U.S. Cl.
CPC ........ *A61M 5/16813* (2013.01); *A61M 39/28* (2013.01); *A61M 39/286* (2013.01); *A61M 39/287* (2013.01); *A61M 5/14228* (2013.01); *A61M 2205/14* (2013.01); *A61M 2205/6018* (2013.01); *A61M 2205/6045* (2013.01); *A61M 2205/6081* (2013.01)

(58) Field of Classification Search
CPC .............. A61M 39/287; A61M 39/286; A61M 5/16813; A61M 39/28
See application file for complete search history.

(56) References Cited

U.S. PATENT DOCUMENTS

| | | | |
|---|---|---|---|
| 4,051,578 A | 10/1977 | Manschot et al. | |
| 4,579,553 A | 4/1986 | Urquhart et al. | |
| 4,586,691 A * | 5/1986 | Kozlow .............. | A61M 39/287 251/7 |
| 4,634,092 A | 1/1987 | Daniell et al. | |
| 4,689,043 A | 8/1987 | Bisha | |
| 5,026,019 A | 6/1991 | Biekart et al. | |

(Continued)

*Primary Examiner* — Bradley J Osinski
(74) *Attorney, Agent, or Firm* — McDermott Will & Emery LLP (57) ABSTRACT

A slide clamp for use with an infusion pump and infusion set provides finger grips and support members for supporting the infusion tubing. The finger grips make the slide clamp easier to use while reducing the risk of error. The tubing support members reduce the likelihood of improperly loading the tubing and reduce the risk of kinking the tubing during use. An infusion set is provided wherein the slide clamp may be coded through the use of colors, holes, or the like so as to identify the type of infusion tubing used therewith. The infusion pump can identify the code on the slide clamp and thereby determine the type of infusion tubing, and thereby allow access only to infusion programs for drugs or infusion solutions which are compatible with the particular type of infusion tubing.

17 Claims, 9 Drawing Sheets

(56) References Cited

U.S. PATENT DOCUMENTS

| | | | |
|---|---|---|---|
| 5,219,327 A | | 6/1993 | Okada |
| 5,232,193 A | * | 8/1993 | Skakoon ............ A61M 5/1418 24/130 |
| 5,257,978 A | | 11/1993 | Haber et al. |
| 5,453,098 A | | 9/1995 | Botts et al. |
| 5,496,846 A | * | 3/1996 | Wilson ................ A61K 31/335 514/449 |
| 5,531,713 A | | 7/1996 | Mastronardi et al. |
| 5,810,323 A | | 9/1998 | Winterer et al. |
| 6,142,979 A | | 11/2000 | McNally et al. |
| 8,403,291 B2 | | 3/2013 | Howlett et al. |
| 2006/0224128 A1 | * | 10/2006 | Lurvey ............ A61M 5/14228 604/250 |
| 2014/0046271 A1 | | 2/2014 | Howlett et al. |

* cited by examiner

METHOD FOR CONTROLLING DRUG DELIVERY THROUGH AN INFUSION SET

RELATED APPLICATIONS

The present application claims the benefit of U.S. Provisional Application Ser. No. 60/936,351, filed Jun. 21, 2007, which is expressly incorporated herein by reference in its entirety.

BACKGROUND OF THE INVENTION

1. The Field of the Invention

The present invention relates to a slide clamp used in conjunction with infusion sets for IV infusion pumps. More specifically, the present invention relates to an improved slide clamp which reduces the possibility of improperly mounting the infusion tubing in the pump and which reduces the possibility of free flow or improper operation of the infusion pump and which is easier to use than available slide clamps.

2. State of the Art

IV infusion pumps are commonly used in treating patients. Infusion pumps deliver a controlled amount of solution such as saline solution and may be used to deliver medication or the like to a patient. An exemplary type of IV infusion pump is the SPECTRUM pump made by SIGMA INTERNATIONAL. Such a linear peristaltic infusion pump will be discussed herein as exemplary of the present invention, as the principles and structures of the present invention will similarly apply to other similar infusion pumps.

IV infusion pumps and infusion sets often include a slide clamp. The slide clamp is part of the infusion set, and interacts with the tubing of the infusion set to selectively prevent free flow through the infusion tubing. The slide clamp typically has a tapered, elongate hole through which the tubing passes. The tubing is not occluded at one end of the hole, and is pinched closed if slid to the other end of the hole. In some cases the slide clamp serves as a key to turn the infusion pump on and off, and may aid in securing the tubing of the infusion set within the pump channel. On some pumps, the slide clamp also serves as a key to open the door of the pump in order to load or unload the infusion tubing. The pump door is unlocked by pressing a portion of the slide clamp into a slot in the body of the pump. Pressing the slide clamp into the slot forces the tubing to the narrow end of the tapered hole, pinching the tubing closed. Thus, the slide clamp provides a measure of safety in preventing free flow as it pinches the tubing closed when the pump door is opened. Slide clamps are often keyed to fit a particular pump, and thus ensure that only compatible infusion sets are used with that pump.

The available slide clamps, however, suffer from several drawbacks. Primarily, the slide clamps do not fix the position of the infusion tube relative to the pump. This leads to potential errors in loading the pump, as the technician loading the pump may place the tubing through the pump in the wrong direction. If the tubing is loaded in the wrong direction, the pump will draw blood from the patient rather than infusing medicament solutions into the patient. It becomes more likely that the infusion tube is improperly loaded in the pump during emergency situations as the medical personnel are in a hurry and are may not be as careful. There are several recorded instances where this type of IV infusion tubing was loaded improperly in the pump and blood was drawn out of the patient.

Additionally, available slide clamps can be difficult to use. The slide clamps are relatively small, and can be difficult for a technician to properly insert and remove from the IV pump. When used as a key for actuating an infusion pump as discussed, the slide clamp may be difficult to remove from the pump as the majority of the slide clamp is encased within the pump. There is thus a need for an improved slide clamp.

SUMMARY OF THE INVENTION

It is an object of the present invention to provide an improved slide clamp for IV infusion pumps.

According to one aspect of the invention, a slide clamp is provided which, when inserted into the pump to open the pump door, holds the tubing in a fixed orientation relative to the pump, orienting the upstream portion of the tubing away from the pump and orienting the downstream portion of the pump across the face of the pump. This places the downstream portion of the tubing in position to be loaded in the pump and significantly reduces the likelihood that the tubing is improperly loaded in the pump.

According to another aspect of the invention, the slide clamp provides integrated handles which are used to more easily insert or remove the slide clamp from the pump body. The handles make it easier to use the slide clamp and reduce the likelihood that the slide clamp is not fully engaged or disengaged during use.

According to another aspect of the invention, the slide clamp provides a tubing support for the tubing which is upstream from the pump. The support helps to prevent kinking of the tubing upstream from the pump while the pump is in use. This, in turn, reduces interruptions in therapy resulting from kinked tubing.

According to another aspect of the invention, a slide clamp is provided which is coded such that the pump is able to identify the type of infusion tubing loaded into the pump by detecting the coding of the slide clamp. The infusion pump may then, based on the type of infusion tubing used, only allow modes of operation which are compatible with the particular type of infusion tube and the drugs or solutions which are compatible with that type of tubing.

These and other aspects of the present invention are realized in a slide clamp as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
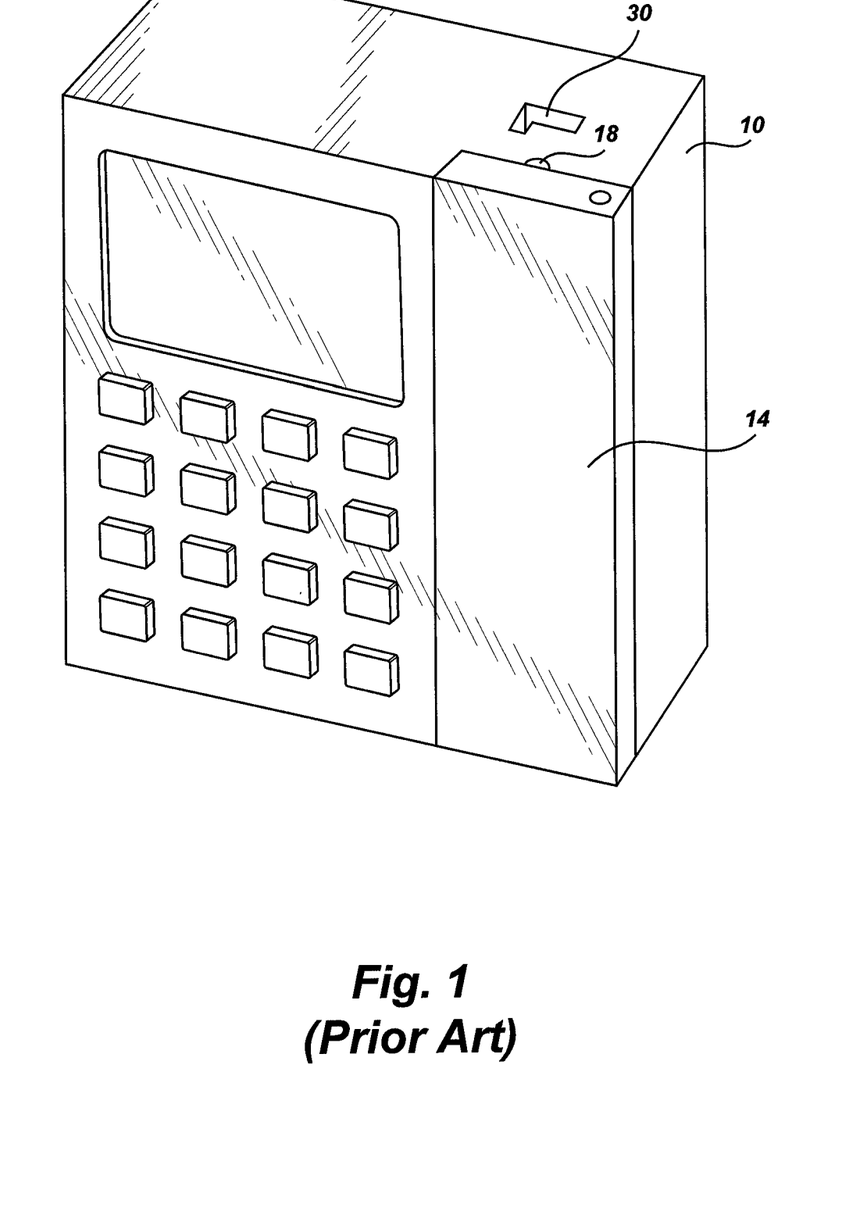
FIG. 1 shows a perspective view of a prior art IV infusion pump.
Figure 2:
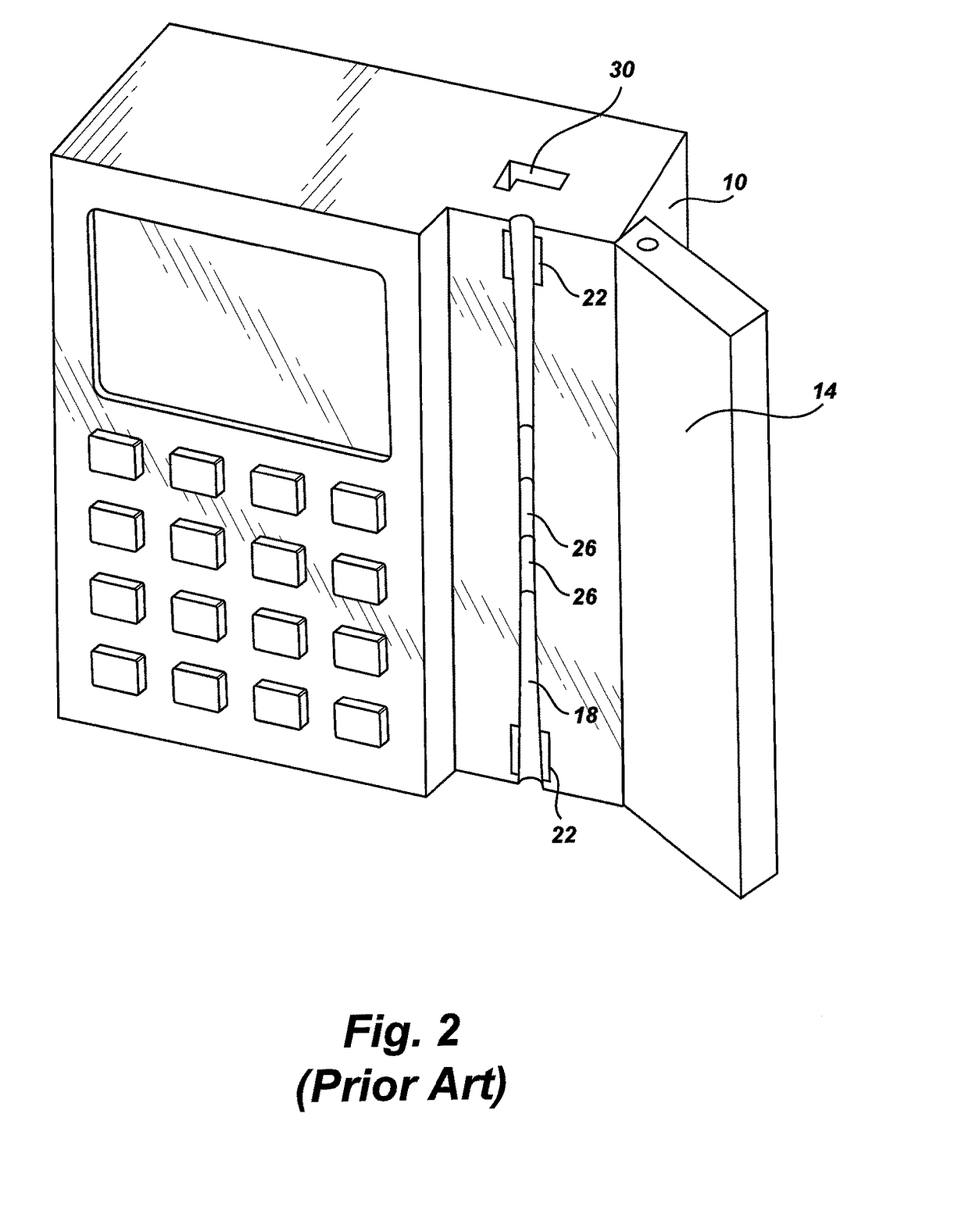
FIG. 2 shows another perspective view of the pump of FIG. 1, the pump door being open.

Turning now to FIG. 1, a perspective view of a linear peristaltic IV pump as is known in the prior art is shown. The pump 10 includes a pump door 14 which holds the infusion tubing into the pump and which holds the tubing against the pumping mechanism. FIG. 2 shows a perspective view of the pump 10, showing the door 14 in an open position. In use, an infusion tubing is loaded into a channel 18 in the pump 10. The channel 18 includes the various sensors or tubing engagement members 22 as well as the pumping members 26 which compress the tubing to force solution therethrough at a controlled rate.

The tubing is loaded into the channel 18 and the pump door 14 is then closed, holding the tubing in the proper location in the pump. The pump 10 has a keyhole slot 30 disposed in the top of the pump. The keyhole 30 receives the slide clamp 34 (FIG. 3), and the slide clamp is inserted fully into the keyhole 30 to open the pump door 14. This prevents the door 14 from being inadvertently opened which in turn releases the tubing from the control of the pumping members. As will be explained in additional detail below, using the slide clamp as a key to open the door 14 causes the slide clamp to occlude flow through the tubing.

Figure 3:
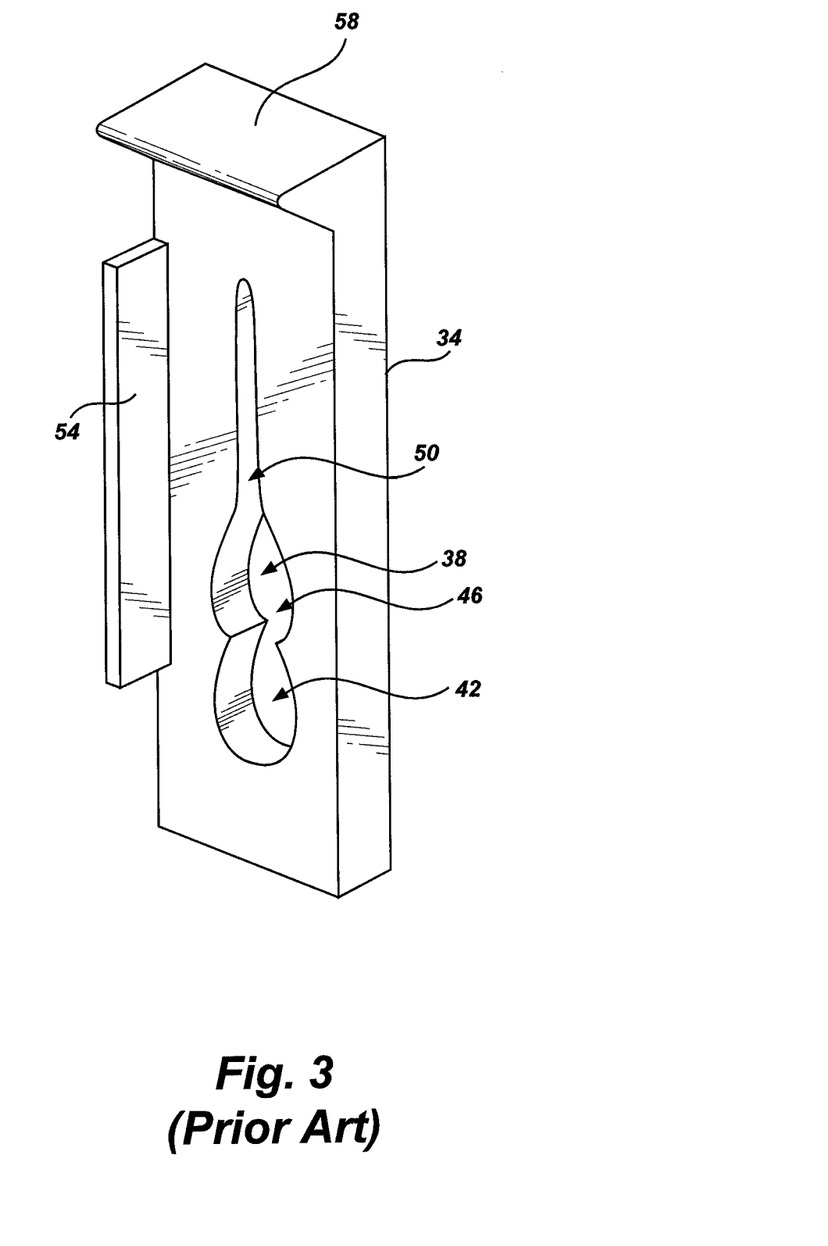
FIG. 3 shows a perspective view of a prior art slide clamp.

FIG. 3 shows the prior art slide clamp 34. The slide clamp 34 includes a slot 38 through which the infusion tubing passes. The slot 38 includes an open lower portion 42 in which the tubing can be initially disposed. The lower portion 42 does not close the tubing. The slot 38 also includes an open middle portion 46 which transitions into a narrow slit 50. The infusion tubing passes transversely through the slot 38. The slide clamp 34 has a raised tab 54 (or alternatively a slot) which allows the slide clamp 34 to only be inserted into the pump 10 in a single orientation. The slide clamp 34 has a small flat head 58 (approximately 0.5 inch wide by 0.2 inch in size) which is used to insert and remove the slide clamp 34 from the pump 10.

When an infusion set is to be used, the slide clamp is typically positioned so the tubing is in the narrow slit 50, thereby occluding flow through the tubing. This prevents a free-flow condition wherein the solution in the infusion set is controlled only by gravity. When the slide clamp 34 is pressed into the keyhole 30 in the pump 10, the tubing is maintained in the narrow slit 50 (or forced into the narrow slit if not yet in this position), pinching the tubing closed. The tubing is pulled back into one of the open portions 42, 46 when the slide clamp 34 is removed from the pump 10. If the pump door is to be opened, the slide clamp 34 must be reinserted into the keyhole 30. This forces the tubing back into the narrow slit 50, thereby occluding the tubing and stopping flow through the tubing and preventing free flow.

Figure 4:
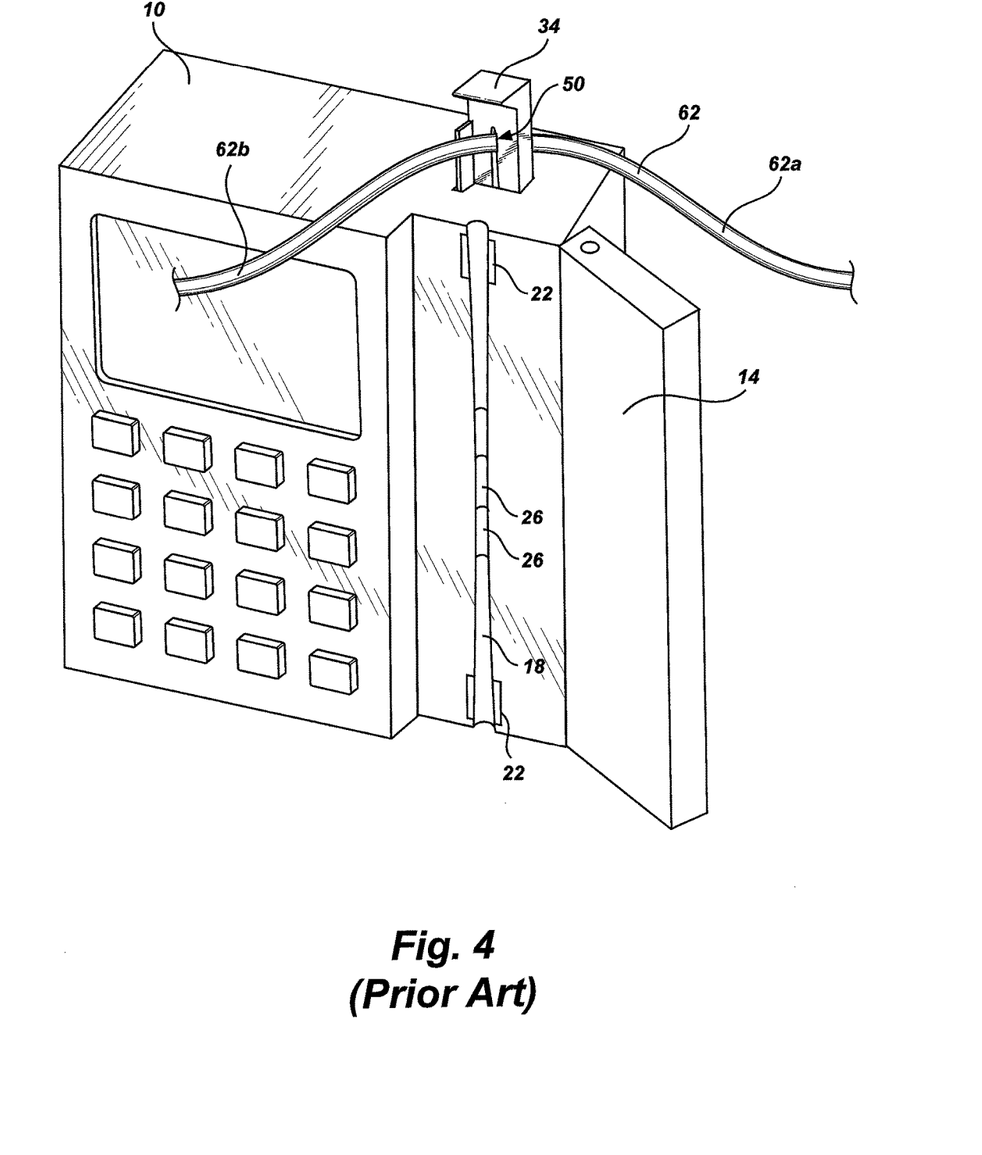
FIG. 4 shows a perspective view of the prior art pump and slide clamp as commonly used together.

Turning now to FIG. 4, a perspective view of the pump 10 and prior art slide clamp 34 with tubing 62 is shown. The slide clamp 34 has been inserted into the keyhole 30 sufficiently far to open the pump door 14. It can be seen how the upper surface of the pump 10 ensures the tubing 62 is in the narrow slit 50, pinching the tubing closed and preventing flow through the tubing while loading the pump. The tubing 62 is then loaded into the pump 10 by pressing the downstream portion 62b of the tubing into the channel 18 and closing the door 14. The tubing 62 is removed from the pump 10 by pressing the slide clamp 34 into the keyhole 30 to again open the door 14, occluding flow through the tubing 62 at the same time by forcing the tubing into the narrow slit 50.

Problems have occurred while loading the tubing 62 into the pump 10. When the tubing 62 is pinched closed by the slide clamp 34, the tubing is easily bent and not held in any repeatable position relative to the pump 10. As a result, the tubing has been improperly loaded into the pump in several instances. In some cases, the upstream portion 62a of the tubing 62 is pulled across the front of the pump 10 or wrapped around the back of the pump and loaded into the channel. Improper loading of the tubing 62 into the pump 10 typically results in improper operation of the pump. In several cases, the tubing 62 was improperly loaded into the pump 10 and the pump then drew blood from the patient and pumped the blood toward the IV bag. This results in both a loss of blood from the patient (potentially serious where a person may have already lost blood in an injury) and in the patient not receiving the fluids or medication which were intended for delivery from the IV bag.

Another limitation of the present pump 10 and infusion tubing 62 and slide clamp 34 is that the tubing may become kinked during operation. The slide clamp 34, by pinching the tubing 62 closed, creates a weak point in the tubing. This weak point or other locations along the tubing 62 may be come kinked or bent closed while the pump is in use. The upstream portion 62a of the tubing 62 is typically long enough to droop below the top of the pump 10 and then extend upwardly to the IV bag, which may result in the tubing 62 bending at the slide clamp 34, pinching the tubing closed at the bend. If the tubing 62 is pinched closed or otherwise bent or kinked, flow of the IV solution to the patient may be compromised.

Figure 5:
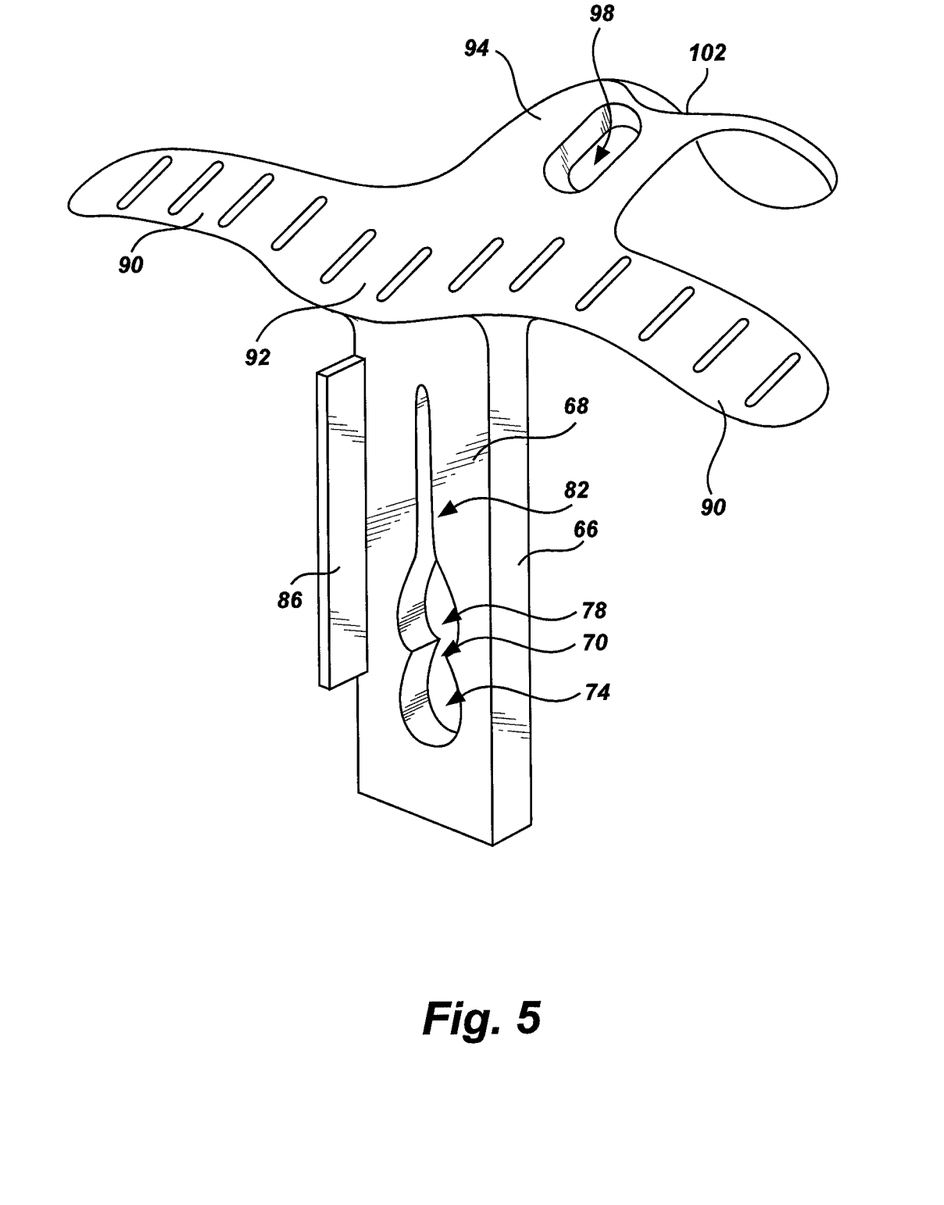
FIG. 5 shows a perspective view of a slide clamp according to the present invention.

Turning now to FIG. 5, a perspective view of a slide clamp 66 according to the present invention is shown. The slide clamp 66 includes a body 68 with a first opening or clamping slot 70 through which the infusion tubing passes. The slot 70 includes an open lower portion 74 in which the tubing is initially disposed. The lower portion 74 does not close the tubing. The slot 70 also includes an open middle portion 78 which transitions into a narrow slit 82. The infusion tubing passes transversely through the slot 70. The slide clamp 66 may include a raised tab 86 (or alternatively a slot or other registration means) which allows the slide clamp 66 to only be inserted into the pump 10 in a single orientation. The lower portion of the slide clamp 66 which is inserted into the pump 10 is configured substantially the same as the prior art slide clamp 34 so that the improved slide clamp 66 will function with the pump in the same manner. Thus, when the slide clamp 66 is pressed into the keyhole 30 in the pump 10, the tubing is forced into the narrow slit 82, pinching the tubing closed. The tubing is pulled back into one of the open portions 74, 78 when the slide clamp 66 is pulled upwardly or removed from the pump 10.

The slide clamp 66 includes two laterally extending finger grips 90 and a rearwardly extending support arm 94. The finger grips 90 provide a place where a user may securely grip the slide clamp 66, making it easier for the user to insert the slide clamp into the keyhole 30 or to remove the slide clamp from the keyhole. The slide clamp 66 may also include a central depression 92 on which a user's thumb would rest. Thus, the top of the slide clamp 66 relative to the body 68 can easily be gripped by the thumb and two fingers for insertion or removal of the slide clamp from the pump 10. The user has greater control over the slide clamp 66 because there is a larger area to grip.

The support arm 94 includes a second opening or support hole 98 through which the infusion tubing passes and a downwardly curving support surface 102 which supports the upstream portion of the tubing during use to prevent kinking of the tubing. Thus, the slide clamp 66 is easier to use and better supports the tubing.

Figure 6:
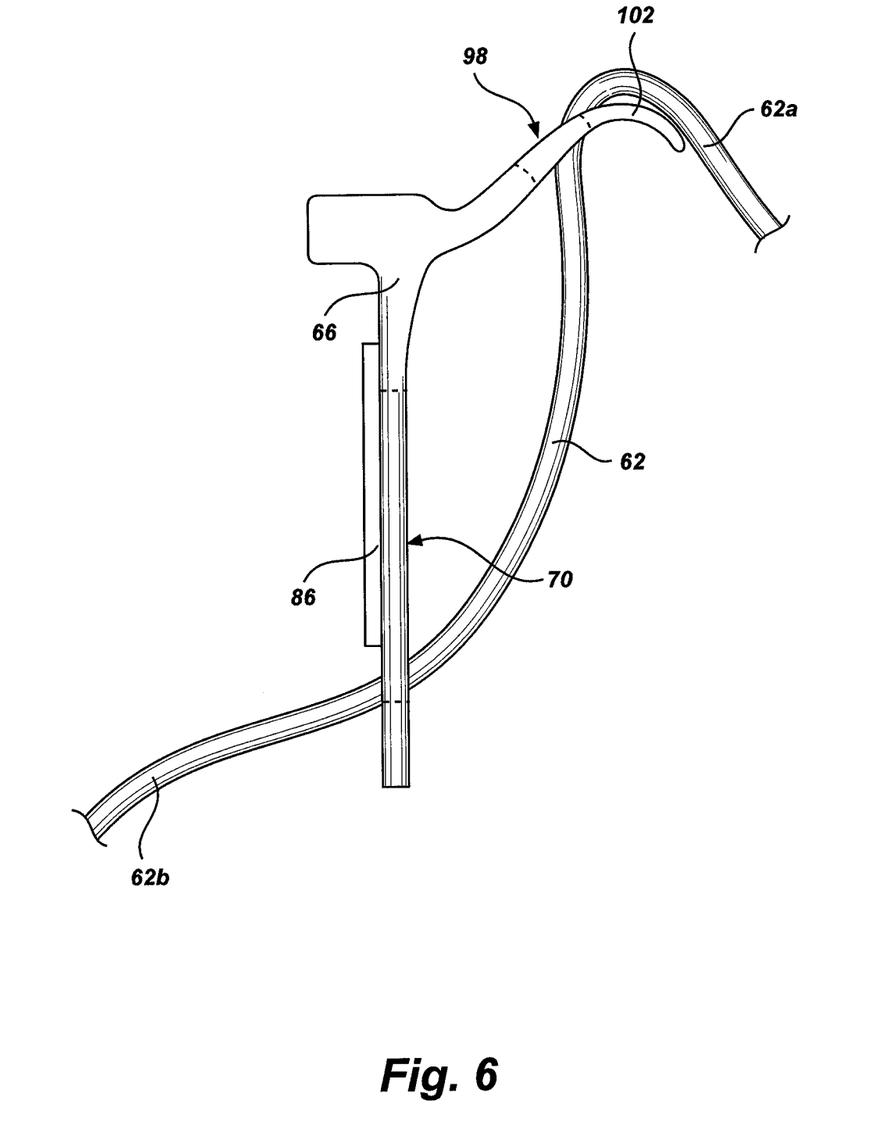
FIG. 6 shows a side view of the slide clamp of FIG. 5 with an infusion tubing.

Turning now to FIG. 6, a partial side view of an infusion set having the slide clamp 66 is shown. It will be appreciated that the infusion set will comprise additional structures such as syringe ports, IV bag spikes, or luer fittings. These additional structures are not discussed herein. It can be seen how the tubing 62 passes through both the clamping slot 70 and the support hole 98. In use, the upstream portion 62a of the tubing 62 can rest on the support surface 102 to prevent the tubing from bending tightly or kinking. Because the tubing passes through the support hole 98, the tubing does not bend adjacent the clamping slot 70. The combination of the clamping slot 70 and the support hole 98 position the tubing so as to make it easier to load the tubing 62 into the pump 10 and to reduce the likelihood of error while loading the tubing.

Figure 7:
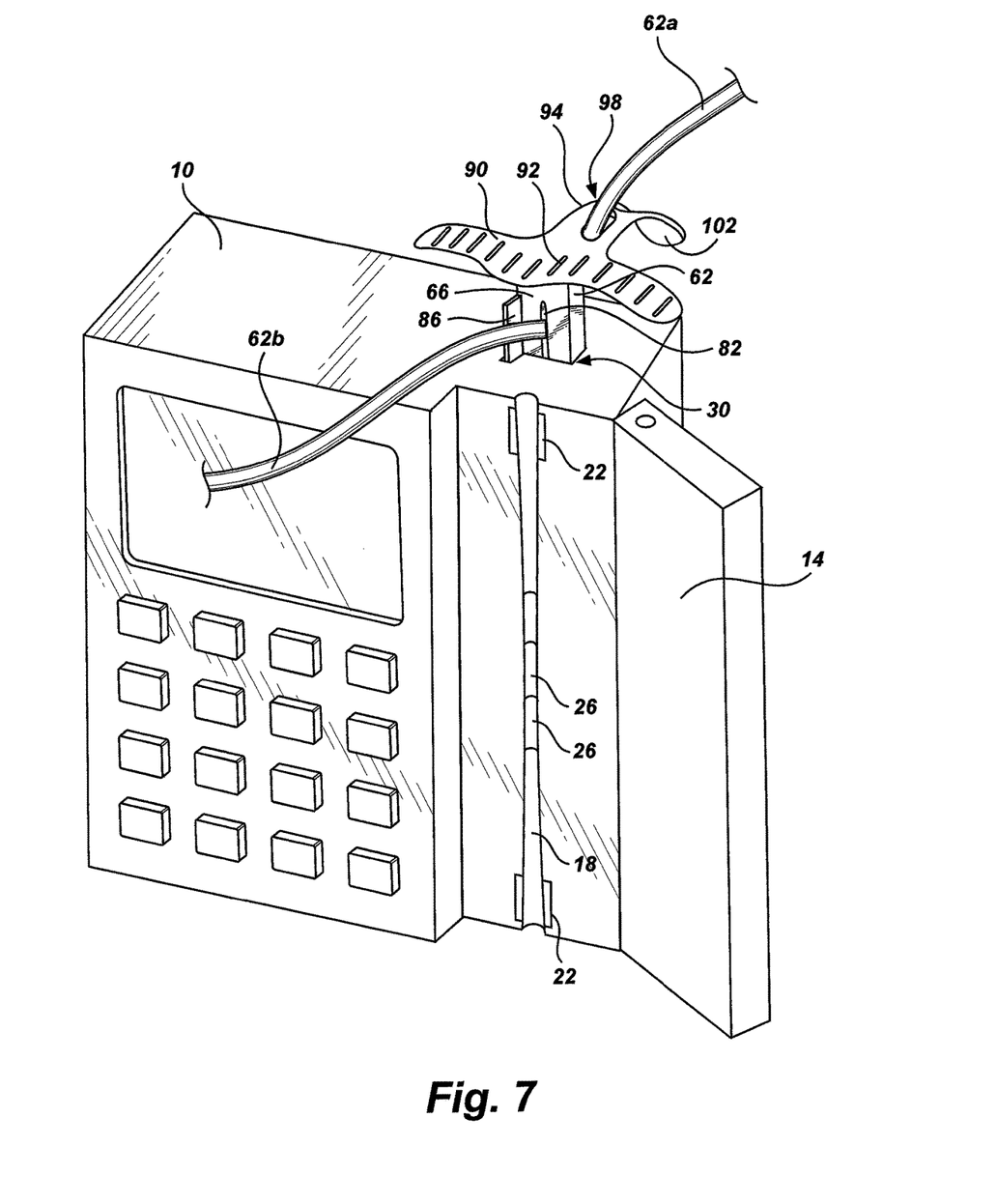
FIG. 7 shows a perspective view of the slide clamp of FIG. 5 in use.

Turning now to FIG. 7, a perspective view of the slide clamp 66 inserted into the pump 10 is shown. The slide clamp 66 is fully inserted into the keyhole 30 to open the pump door, simultaneously ensuring the tubing 62 is pressed into the narrow slit 82 and pinching the tubing closed to prevent flow. As is seen, the upstream portion 62a of the tubing 62 passes through the support hole 98 and is held by the support arm 94 so that the upstream portion of the tubing extends upwardly and away from the pump 10. It will be appreciated that, even if the slide clamp does not include a registration means 86, the risk of misleading the tubing is reduced since the upstream portion 62a of the tubing 62 is held so that it extends upwardly and away from the pump channel 18. By holding the upstream portion 62a of the tubing 62 upwardly and away from the pump 10 and holding the upstream portion of the tubing away from the channel 18, a user is much less likely to improperly load the tubing into the pump.

The finger grips 90 and depression 92 for the thumb make it significantly easier to use the slide clamp 66. It will be appreciated that the tubing 62 fits tightly into the narrow slit 82 in order to securely pinch the tubing closed. As such, a fair amount of force is required when inserting the slide clamp 66 into the keyhole 30. Additionally, when removing the slide clamp 66 from the keyhole 30, the user often desires to hold the tubing 62 against the pump 10 while pulling the slide clamp from the keyhole 30 to ensure that the tubing adjacent the pumping members is not unduly stretched or displaced. Again, a fair amount of force is required in addition to the fact that the user may desire to use both hands in removing a slide clamp. It can thus be understood how the finger grips 90 make it significantly easier for a person to insert and remove the slide clamp 66.

Figure 8:
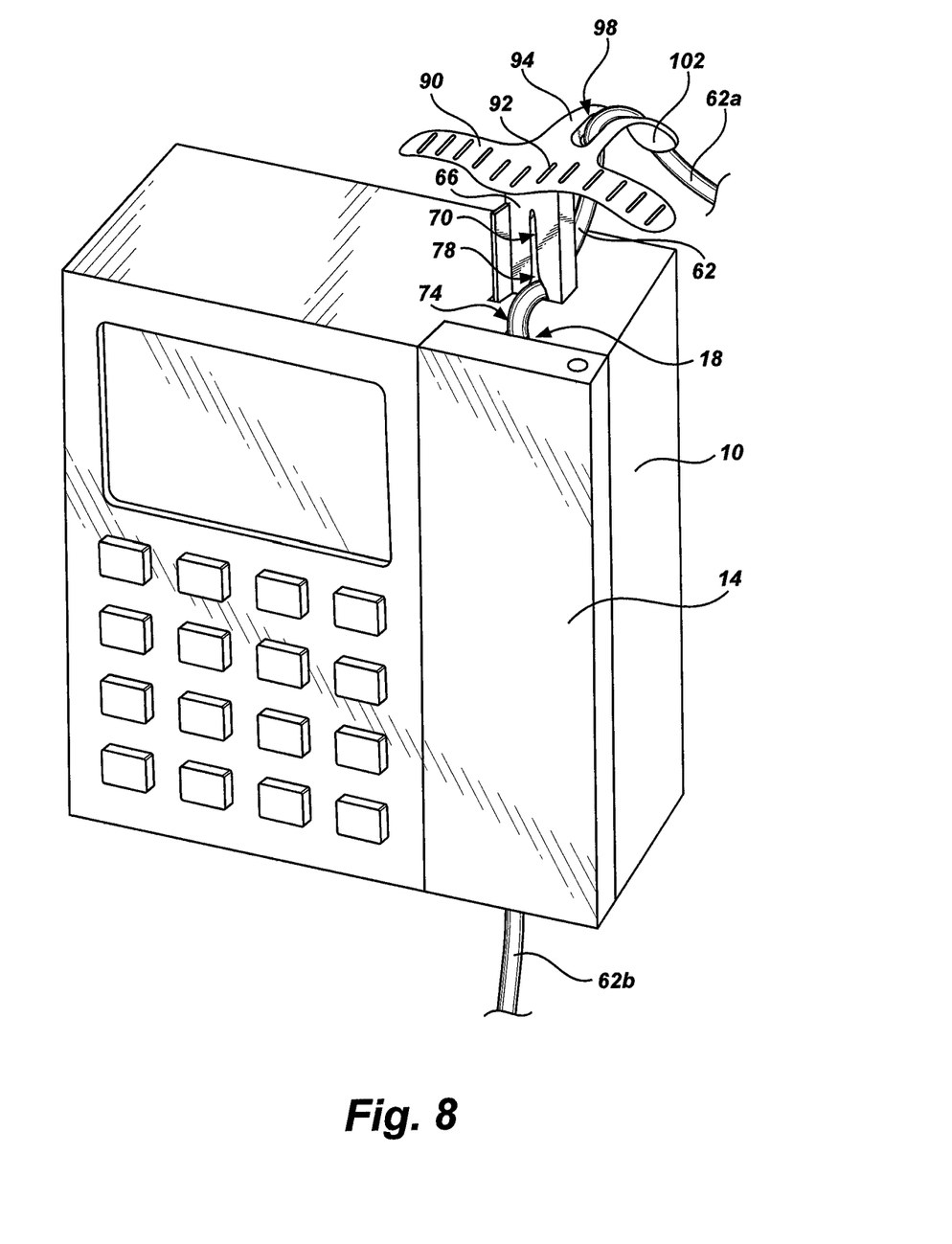
FIG. 8 shows another perspective view of the slide clamp of FIG. 5 in use.

The slide clamp 66 also reduces the risk that the tubing 62 is kinked while in use. Medical personnel may be instructed to leave the slide clamp 66 partially inserted (about 0.25 inch or less) into the keyhole 30 so that the slide clamp 66 will typically be left partially in the keyhole 30. FIG. 8 shows such as configuration, where the infusion tubing 62 has been loaded into the pump 10 and the slide clamp 66 has been withdrawn sufficiently to place the tubing 62 into one of the open portions 74, 78 of the clamping slot 70. The upstream portion 62a of the tubing 62 passes through the support hole 98 in the support arm 94. As such, the slide clamp 66 helps to prevent kinking or undesired bending of the tubing 62. The support hole 98 holds the upstream portion 62a of the tubing 62 so that the tubing is not undesirably bent near the clamping slot 70.

As mentioned, this area of the tubing 62 is weakened by being pinched closed by the clamping slot 70. The tubing is not bent at the clamping slot as the downstream portion 62b is held in place in the pump channel 18 and the upstream portion 62a is held in place by the support hole 98. The curved support surface 102 gradually bends downwardly away from the support hole 98 so that if the upstream portion of the tubing 62a hangs below the top of the pump as shown, the curved support surface prevents the tubing from being kinked or tightly bent at the support hole 98. It is thus observed that the slide clamp 66 significantly reduces the likelihood that the tubing 62 is kinked or collapsed near the pump 10.

Different infusion sets (having different types of tubing) may be used according to the fluid which is being delivered to the patient. For example, nitroglycerine is used with infusion tubing having a poly lining to prevent the nitroglycerine from being absorbed into the vinyl tubing or otherwise interacting with the tubing and interfering with the infusion process. Similarly, the taxol drug uses a poly lined tubing so that the drug solution does not leach plasticizing agents out of the vinyl tubing. Epidural tubing has an anti kink delivery portion downstream of the pumping portion of the tubing. Thus, various types of infusion tubing have specific uses and should not be used with the wrong types of infusion solutions.

According to another aspect of the invention, the slide clamp 66 may be coded according to the intended usage of the tubing 62 to select the operational mode of the pump 10 when the clamp is inserted into the pump. An IV pump 10 may be used which contains an optical sensor disposed in communication with the keyhole 30. The slide clamps 66 may be made in different colors, each color being used with a particular type of infusion tubing 62. When a slide clamp 66 is inserted into the keyhole 30, the pump 10 may, via the optical sensor, determine what color the slide clamp is and only allow access to the operational modes of the pump which are compatible with the infusion tubing. The infusion pumps 10 often include drug libraries stored in their memory. When the slide clamp 66 is inserted into the infusion pump 10, the pump may only allow the medical personnel to select drugs and access infusion programs for the drugs which are compatible with the infusion tubing which has been loaded into the pump. Thus, the medical personnel would not be able to access the infusion programs within the pump 10 for drugs or infusion solutions which are not compatible with the tubing which has been loaded into the pump.

Figure 9:
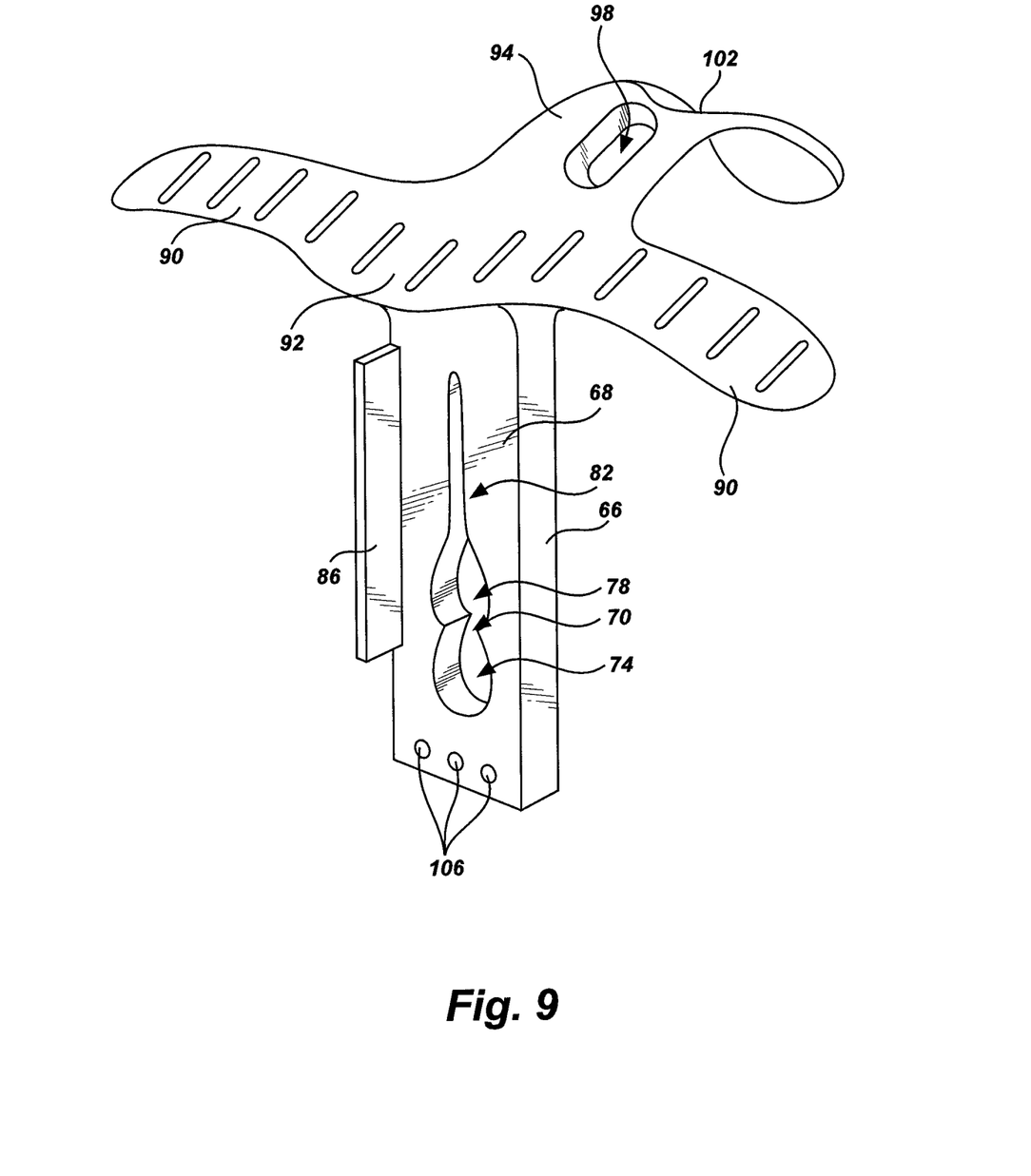
FIG. 9 shows another perspective view of the slide clamp of FIG. 5.

Alternatively, the slide clamp 66 may be formed with small projections or recesses, or one or more identification holes 106 formed through the side or bottom thereof as indicated in FIG. 9. The pump 10 may have an optical emitter/detector pair disposed in communication with the keyhole 30 to sense the number of holes 106 or the position of the holes 106 and thereby detect the type of infusion set which is being loaded into the pump and allow the operational modes of the pump which are compatible with the infusion set. It will be appreciated that the slide clamp 66 of FIG. 9 which includes holes 106 or color coding is otherwise used as discussed above with respect to FIGS. 5 through 8.

There is thus disclosed an improved slide clamp for IV pumps. It will be appreciated that numerous changes may be made to the present invention without departing from the scope of the claims.

What is claimed is:

1. A method for preventing misloading and kinking of an infusion tube, the method comprises;
    selecting an infusion set, the infusion set comprising an infusion tube and a slide clamp disposed on the infusion tube, the slide clamp having a clamping slot configured for selectively occluding the infusion tube and a separate support opening, the support opening being spaced apart from the clamping slot, and wherein the infusion tube passes through the clamping slot and through the support opening; and
    inserting the slide clamp into an infusion pump so that an upstream portion of the infusion tube rests on the support opening upwardly and rearwardly away from the pump, and at least partially withdrawing the slide clamp so that the slide clamp does not occlude flow through the infusion tube.

2. The method according to claim 1, wherein the method comprises selecting a slide clamp having a body containing the clamping slot and a support arm containing the support opening and extending at an angle away from the body so that the infusion tube does not extend generally perpendicular to the clamping slot.

3. The method according to claim 1, wherein the method comprises selecting the slide clamp with a pair of finger grips and inserting the slide clamp into the infusion pump while holding onto the finger grips.

4. The method according to claim 3, wherein the pair of finger grips includes finger grips disposed on opposing sides of the slide clamp.

5. The method according to claim 4, wherein the slide clamp further comprises a depression between the finger grips.

6. The method according to claim 1, wherein the method further comprises:
    selecting a slide clamp which is coded such that the infusion pump may optically identify the slide clamp and thereby identify the type of infusion tube used therewith;
    the infusion pump optically identifying the slide clamp when the slide clamp is inserted into the infusion pump; and
    the infusion pump selectively allowing access to modes of operation which are compatible with the type of infusion tube.

7. The method according to claim 6, wherein the slide clamp is color coded and wherein the infusion pump optically detects a color on the slide clamp to thereby detect the type of infusion tube used with the slide clamp.

8. The method according to claim 6, wherein the slide clamp comprises at least one hole therethrough, and wherein the infusion pump detects the configuration of the at least one hole to identify the type of infusion tube used therewith.

9. A method for controlling fluid flow through an infusion tube, the method comprising:
    selecting a slide clamp having a body, a clamping slot formed through the body, the clamping slot having an open end configured for receiving an infusion tube without closing the infusion tube and a narrow slit extending from the open end, the narrow slit being sufficiently thin to close the infusion tube when the infusion tube is disposed therein, and a support arm extending from the body, the support arm having a hole for receiving an upstream portion of the infusion tube and a support surface, and an infusion tube passing through the clamping slot and the hole in the support arm, the slide clamp being coded in a manner detectable by an infusion pump in a manner to identify characteristics of the infusion tube; and
    inserting the slide clamp into a pump such that (i) the upstream portion of the infusion tube rests on the support surface upwardly and rearwardly away from the pump, and (ii) the pump detects the slide clamp inserted and selects operational modes of the pump which are compatible with slide clamp detected.

10. The method of claim 9, wherein the method comprises optically detecting the slide clamp to determine which operational modes should be selected.

11. The method of claim 9, wherein the slide clamp has one or more holes and wherein the pump detects at least one of position and number of holes to determine which operational modes should be selected.

12. The method according to claim 9, wherein the slide clamp is color coded based on the infusion tube disposed therein and wherein the pump detects the color of the slide clamp and limits infusion programs available to infusion programs for drugs which are compatible with the infusion tube disposed in the slide clamp.

13. The method according to claim 12, wherein the infusion tube is a poly lined tube and wherein the operational modes of the pump includes an operational mode for any of a nitroglycerin drug and a taxol drug.

14. A method for improving drug delivery, the method comprises:
    selecting an infusion tubing having a desired characteristic for one or more drugs; and
    disposing a portion of the infusion tubing in a clamp having a clamping slot, a support opening, and a visual indicia associated with the desired characteristic of the infusion tubing, wherein a downstream portion of the infusion tubing is disposed through the clamping slot and an upstream portion of the infusion tubing is disposed through the support opening spaced apart from the clamping slot; and
    inserting the clamp into an infusion pump so that the upstream portion of the infusion tubing rests on the support opening upwardly and rearwardly away from the pump.

15. The method according to claim 14, wherein the visual indicia is a color.

16. The method according to claim 14, wherein the visual indicia comprises at least one hole in the clamp and wherein a location of the at least one hole or a number of holes indicates the infusion tube disposed in the clamp.

17. The method according to claim 14, wherein the method comprises inserting the clamp into a pump so that the pump detects the visual indicia and the pump selecting one or more operating modes based on the visual indicia.

* * * * *